United States Patent [19]
Austel et al.

[11] 4,176,184
[45] Nov. 27, 1979

[54] IMIDAZOISOQUINOLINE-DIONES AND SALTS THEREOF

[75] Inventors: Volkhard Austel; Eberhard Kutter, both of Biberach; Joachim Heider, Warthausen; Wolfgang Eberlein, Biberach, all of Fed. Rep. of Germany; Walter Kobinger; Christian Lillie, both of Vienna, Austria; Willi Diederen; Walter Haarmann, both of Biberach, Fed. Rep. of Germany

[73] Assignee: Boehringer Ingelheim GmbH, Ingelheim am Rhein, Fed. Rep. of Germany

[21] Appl. No.: 925,461

[22] Filed: Jul. 17, 1978

[30] Foreign Application Priority Data

Jul. 21, 1977 [DE] Fed. Rep. of Germany ....... 2732906
Jul. 21, 1977 [DE] Fed. Rep. of Germany ....... 2732951

[51] Int. Cl.² .................. A61K 31/535; C07D 471/04
[52] U.S. Cl. .......................... 424/248.52; 424/248.57; 424/250; 424/256; 544/126; 544/361; 546/82; 546/142
[58] Field of Search .................. 546/82; 544/126, 361; 424/248.52, 256, 250, 248.57

[56] References Cited

U.S. PATENT DOCUMENTS

| | | | |
|---|---|---|---|
| 3,878,206 | 4/1975 | Spencer | 260/247.5 EP |
| 3,919,238 | 11/1975 | Spencer | 260/288 CF |

*Primary Examiner*—Donald G. Daus
*Assistant Examiner*—Lisa Jones
*Attorney, Agent, or Firm*—Hammond & Littell

[57] ABSTRACT

Compounds of the formula

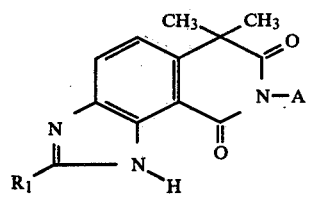

wherein
$R_1$ is lower alkyl; phenyl-lower alkyl; cycloalkyl of 3 to 6 carbon atoms; phenyl; mono- or di-substituted phenyl, where the substituents, which may be identical to or different from each other, are each halogen, hydroxyl, methoxy, methylmercapto, methylsulfinyl, methylsulfonyl or benzyloxy; and
A is hydrogen or

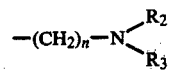

where
$R_2$ is hydrogen or lower alkyl;
$R_3$ is lower alkyl or dimethoxyphenyl-lower alkyl; or
$R_2$ and $R_3$, together with each other and the nitrogen atom to which they are attached, are piperidino, morpholino or N'-lower alkyl-piperazino; and
n is 2 or 3;

and non-toxic, pharmacologically acceptable acid addition salts thereof. The compounds as well as their salts are useful as cardiotonics, hypotensives, antithrombotics and antiarrhythmics.

12 Claims, No Drawings

IMIDAZOISOQUINOLINE-DIONES AND SALTS THEREOF

This invention relates to novel imidazoisoquinoline-diones and acid addition salts thereof, as well as to methods of preparing these compounds, pharmaceutical compositions containing them, and methods of using them as cardiotonics, hypotensives, antithrombotics, and antiarrhythmics.

More particularly, the present invention relates to a novel class of imidazoisoquinoline-diones represented by the formula

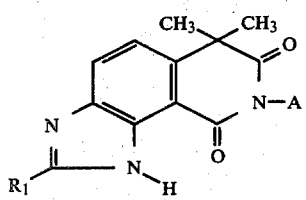   (I)

wherein
$R_1$ is lower alkyl, phenyl-lower alkyl, cycloalkyl of 3 to 6 carbon atoms; phenyl; mono- or di-substituted phenyl, where the substituents, which may be identical to or different from each other, are each halogen, hydroxyl, methoxy, methylmercapto, methylsulfinyl, methylsulfonyl or benzyloxy; and
A is hydrogen or

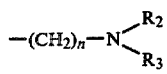

where
$R_2$ is hydrogen or lower alkyl;
$R_3$ is lower alkyl or dimethoxyphenyl-lower alkyl; or
$R_2$ and $R_3$, together with each other and the nitrogen atom to which they are attached, are piperidino, morpholino or N'-lower alkyl-piperazino; and
n is 2 or 3;
and non-toxic, pharmacologically acceptable acid addition salts thereof.

The term "lower alkyl" used in the definition of substituents $R_1$, $R_2$ and $R_3$ of formula I is intended to designate alkyl of 1 to 6 carbon atoms, preferably alkyl of 1 to 3 carbon atoms, and the term "halogen" used in the definition of $R_1$ is primarily intended to mean chlorine, fluorine or bromine.

Thus, specific exemplary embodiments of the various substituents in formula I are the following.

R—methyl, ethyl, propyl, isopropyl, cyclopropyl, cyclobutyl, cyclopentyl, cyclohexyl, benzyl, 1-phenylethyl, 1-phenyl-propyl, 2-phenylethyl, 2-phenylpropyl, 3-phenylpropyl, 3-phenyl-2-propyl, phenyl, methoxyphenyl, dimethoxyphenyl, chlorophenyl, dichlorophenyl, fluorophenyl, difluorophenyl, hydroxyphenyl, dihydroxyphenyl, bromophenyl, dibromophenyl, chloro-bromophenyl, methylmercaptophenyl, bismethylmercaptophenyl, methylsulfinyl-phenyl, bismethylsulfinylphenyl, methylsulfonylphenyl, bismethylsulfonylphenyl, benzyloxyphenyl, dibenzyloxyphenyl, hydroxymethoxyphenyl, hydroxy-methylmercaptophenyl, hydroxy-methylsulfinylphenyl, hydroxy-methylsulfonyl-phenyl, hydroxy-benzyloxyphenyl, hydroxy-chlorophenyl, hydroxybromophenyl, methoxy-methyl-mercaptophenyl, methoxy-methylsulfinylphenyl, methoxy-methylsulfonylphenyl, methoxy-benzyloxphenyl, methoxy-chlorophenyl, methoxy-fluorophenyl, methoxy-bromophenyl, methylmercapto-methylsulfinylphenyl, methylmercapto-methylsulfonylphenyl, methylmercaptobenzyloxyphenyl, methylmercaptochlorophenyl, methyl-mercapto-bromophenyl, methylsulfinyl-methylsulfonylphenyl, methyl-sulfinyl-chlorophenyl, methylsulfinyl-bromophenyl, methyl-sulfinyl-benzyloxphenyl, methylsulfonyl-chlorophenyl, methylsulfonyl-bromophenyl or methylsulfonyl-bromophenyl;

$R_2$—hydrogen, methyl, ethyl, propyl or isopropyl;
$R_3$—methyl, ethyl, propyl, isopropyl, dimethoxybenzyl, 1-(dimethoxyphenyl)-ethyl, 2-(dimethoxyphenyl)-ethyl, 3-(dimethoxyphenyl)-propyl or 3-(dimethoxyphenyl)-2-propyl; and
$R_2$ and $R_3$, together with each other and the nitrogen atom to which they are attached—piperidino, morpholino, N'-methyl-piperazino, N'-ethyl-piperazino, N'-propyl-piperazino or N'-isopropyl-piperazino.

A preferred sub-genus under the genus of formula I is constituted by those compounds where
$R_1$ is methyl, ethyl, benzyl, 1-phenylethyl, 2-phenylethyl, cyclopropyl, cyclohexyl, 4-chlorophenyl, 2-methoxy-5-methyl-sulfinyl-phenyl, 2-methoxy-5-methylsulfonylphenyl, or phenyl which may be mono or disubstituted in the 2- and/or 4-position by methoxy, hydroxyl, methylmercapto, methylsulfinyl and/or methylsulfonyl; and
A is hydrogen or

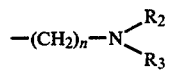

where
$R_2$ is hydrogen, methyl, ethyl or propyl,
$R_3$ is methyl, ethyl, propyl or 2-(3,4-dimethoxyphenyl)ethyl, or
$R_2$ and $R_3$, together with each other and the adjacent nitrogen atom, are piperidino, morpholino or N-methyl-piperazino, and
n is 2 or 3.

The compounds embraced by formula I may be prepared by the following methods:

Method A

By reacting a dicarboxylic acid of the formula

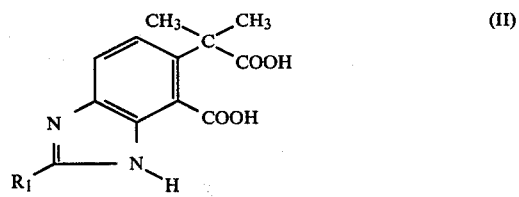   (II)

wherein $R_1$ has the same meanings as in formula I, or a reactive derivative thereof such as an anhydride, ester, amide, imide or halide, with an amine of the formula

   (III)

wherein A has the same meanings as in formula I.

The reaction is carried out, depending on the reactivity of the reactive derivative of compound II, at temperatures between 50° and 250° C., optionally in a solvent such as tetralin or ethylene glycol, but preferably in the molten state. If a carboxylic acid of the formula II is used, the the reaction is preferably carried out at the boiling point of ethylene glycol. However, the reaction may also be carried out with a corresponding ammonium salt of a carboxylic acid of the formula II or with the corresponding amide at elevated temperatures, optionally in the presence of a dehydrating agent such as hydrochloric acid, sulfuric acid, p-toluenesulfonic acid or phosphorus oxychloride.

Method B

For the preparation of a compound of the formula I, wherein A is other than hydrogen, by reacting an isoquinoline-dione of the formula

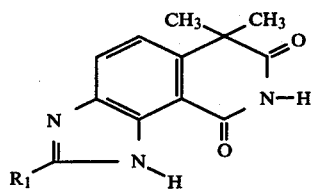

(IV)

wherein $R_1$ has the same meanings as in formula I, or an alkali metal salt thereof, with an amine of the formula

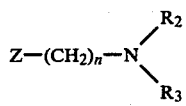

(V)

wherein
$R_2$, $R_3$ and n have the same meanings as in formula I, and
Z is an exchangeable substituent such as chlorine, bromine, iodine or a sulfonyloxy group, especially p-toluenesulfonyloxy.

The reaction is advantageously carried out in an inert solvent such as dimethylsulfoxide or dimethylformamide, in the presence of an alkali metal base such as sodium hydride, sodium amide or potassium-tert. butoxide, and at temperatures between 0° and 200° C., but preferably at temperatures between 20° and 160° C. However, the reaction may also be carried out without a solvent.

Method C

For the preparation of a compound of the formula I wherein A is other than hydrogen, by reacting an isoquinoline-dione of the formula

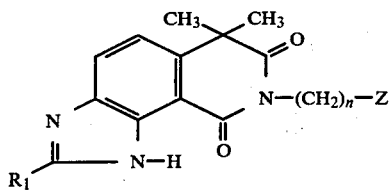

(VI)

wherein
$R_1$ and n have the same meanings as in formula I, and
Z is an exchangeable substituent such as chlorine, bromine, iodine or a sulfonyloxy group, especially p-toluenesulfonyloxy,
with an amine of the formula

(VII)

wherein $R_2$ and $R_3$ have the same meanings as in formula I.

The reaction is advantageously carried out in a solvent such as dioxane, dimethylsulfoxide, dimethylformamide or tetralin, optionally in the presence of an inorganic base such as sodium carbonate or potassium carbonate, or a tertiary organic base such as triethyl amine, pyridine or collidine, or in the presence of an excess of the amine of the formula VII, at temperatures between 50° and 200° C., preferably at the boiling point of the reaction mixture, for example, at temperatures from 100° to 160° C. A tertiary organic base and/or an excess of the amine of the formula VII may simultaneously serve as the solvent. However, the reaction may also be carried out without a solvent.

Method D

For the preparation of a compound of the formula I wherein A is hydrogen, by reducing an 8-nitro-isoquinoline-dione of the formula

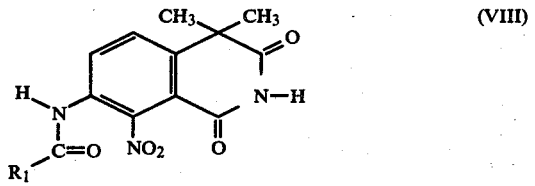

(VIII)

wherein $R_1$ has the same meanings as in formula I, and subsequently cyclizing the 8-amino-isoquinoline-dione reduction product of the formula

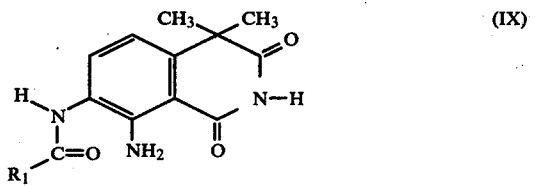

(IX)

wherein $R_1$ has the meanings previously defined, in the presence of an acid condensation agent.

The reduction of the compound of the formula VIII is advantageously carried out in a solvent such as methanol, ethanol, ethyl acetate, water, water/isopropanol, dimethylformamide or glacial acetic acid, with nascent or catalytically activated hydrogen or with tin-II-chloride/hydrochloride acid, hydrazine/Raney nickel, iron-II-sulfate or zinc/glacial acetic acid at temperatures between 0° and 150° C., preferably at temperatures between 20° and 80° C. The subsequent cyclization of the compound of the formula IX, which is preferably not isolated, is effected at elevated temperatures, preferably at the boiling point of the reaction mixture, in the presence of an acid condensation agent, such as hydrochloric acid, sulfuric acid, p-toluene sulfonic acid or phosphorus oxychloride.

The reduction with nascent hydrogen is preferably carried out with zinc/glacial acetic acid or iron/hydrochloric acid at temperatures between 20° and 80° C. The catalytic reduction is preferably carried out with hydrogen in the presence of a catalyst, such as palladium/charcoal, preferably at a hydrogen pressure of 3 to 7 atmospheres and at temperatures between 20° and 80° C.

In those instances where methods A to D yield a compound of the formula I wherein $R_1$ is methylmercapto-phenyl, this compound can be converted into the corresponding methylsulfinyl- or methylsulfonyl-phenyl substituted compound of the formula I with one or two equivalents of an oxidizing agent, respectively. Likewise, a compound of the formula I wherein $R_1$ is methylsulfinyl-phenyl can be converted into the corresponding methylsulfornyl-phenyl substituted compound by treatment with an oxidizing agent. Finally, a compound of the formula I wherein $R_1$ is benzyloxy-phenyl can be converted into the corresponding hydroxy-phenyl substituted compound by de-benzylation.

The oxidations referred to in the preceding paragraph are advantageously carried out in a solvent such as glacial acetic acid or water/glacial acetic acid, with an oxidizing agent such as hydrogen peroxide, optionally in the presence of an alkali metal acetate such as sodium acetate, at temperatures between 0° and 100° C., preferably at temperatures between 10° and 50° C.

The de-benzylation is advantageously carried out in a solvent such a methanol or ethyl acetate, with catalytically activated hydrogen, for example with hydrogen in the presence of palladium/charcoal at a hydrogen pressure of 3 to 6 atmospheres and at temperatures between 40° and 60° C.

The starting compounds for methods A to D are either known compounds or may be prepared by methods described in the literature. For example, a compound of the formula II or IX is obtained by condensation of a corresponding acylaminoamino compound, or a compound of the formula VI is obtained by reaction of a corresponding isoquinoline-dione with a corresponding halogen compound.

The compounds embraced by formula I are organic bases and therefore form additional salts with inorganic or organic acids. Examples of non-toxic, pharmacologically acceptable acid addition salts are those formed with, for example, hydrochloric acid, hydrobromic acid, sulfuric acid, phosphoric acid, lactic acid, citric acid, furmaric acid, furmaric acid, maleic acid or the like.

The following examples illustrate the present invention and will enable others skilled in the art to understand it more completely. It should be understood, however, that the invention is not limited solely to the particular examples given below.

EXAMPLE 1

7,7-Dimethyl-2-phenyl-5H,7H-imidazo[4,5-h]isoquinoline-4,6-dione hydrochloride by method D (a) 220 gm of 4,4-dimethyl-7-acetamino-2H,4H-isoquinoline-1,3-dione were added in portions to 800 ml of fuming nitric acid at −20° C. while stirring. The mixture was stirred for one hour at this temperature. Then, the reaction mixture was poured over ice, the precipitate was suction-filtered off, washed neutral with water, dried in the air, and boiled with isopropanol. After cooling, the crystals were suction-filtered off and washed with ether, yielding 222 gm (85% of theory) of 4,4-dimethyl-7-acetamino-8-nitro-2H,4H-isoquinoline-1,3-dione, m.p. 249° C. (decomp.).

(b) 43.8 gm of 4,4-dimethyl-7-acetamino-8-nitro-2H,4H-isoquinoline-1,3-dione were admixed with 200 gm of xylene with 104 gm of benzoyl chloride, and the mixture was refluxed for 10 hours while stirring. After cooling, the reaction mixture was suction-filtered, and the filter cake was washed with toluene and petroleum ether, yielding 36 gm (68% of theory) of 4,4-dimethyl-7-benzoylamino-8-nitro-2H,4H-isoquinoline-1,3-dione, m.p. above 270° C.

(c) 17.6 gm of 4,4-dimethyl-7-benzoylamino-8-nitro-2H,4H-isoquinoline-1,3-dione were hydrogenated in 1200 ml of methanol in the presence of 1.5 gm of 10% palladium-on-charcoal at 50° C. and at a hydrogen pressure of 5 atmospheres for 8 hours. The resulting solution of 4,4-dimethyl-7-benzoylamino-8-amino-2H,4H-isoquinoline-1,3-dione was admixed with 300 ml of saturated methanolic hydrochloric acid and refluxed for 3 hours. The catalyst was then suction-filtered off, the filtrate was evaporated to 100 ml and admixed with 100 ml of ether, and the precipitated product was suction-filtered off and washed with ether, yielding 14.8 gm (86.5% of theory) of the compound of the formula

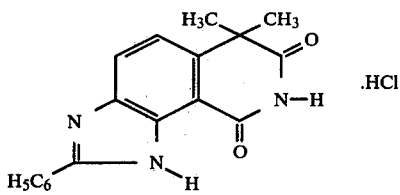

which had a melting point above 260° C.

EXAMPLE 2

7,7-Dimethyl-2-(2,4-dimethoxy-phenyl)-5H,7H-imidazo[4,5-h]isoquinoline-4,6-dione hydrochloride by method D (a) 4,4-Dimethyl-7-(2,4-dimethoxybenzoyl amino)-8-nitro-2H,4H-isoquinoline-1,3-dione 2.7 gm of 4,4-dimethyl-7-amino-8-nitro-2H,4H-isoquinoline-1,3-dione were admixed with 50 ml of chloroform and 2.5 ml of triethylamine. Subsequently, 2.2 gm of 2,4-dimethoxybenzoylchloride were added, and the mixture was refluxed for 2 hours. After cooling the solution was evaporated and the precipitate was suction-filtered off and digested with water while heating.

Yield: 3.2 gm(71.1% of theory); M.p. above 250° C.

(b) 7,7-Dimethyl-2-(2,4-dimethoxy-phenyl)-5H,7H-imidazo[4,5-h]-isoquinoline-4,6-dione hydrochloride Prepared analogous to Example 1c from 3.1 gm of 4,4-dimethyl-7-(2,4-dimethoxybenzoyl amino)-8-nitro-2H,4H-isoquinoline-1,3-dione.

Yield: 2.1 gm (74.7% of theory); M.p. 248°–249° C.

EXAMPLE 3

7,7-Dimethyl-2-(2-methoxy-4-methylmercapto-phenyl)-5H,7H-imidazo[4,5-h]isoquinoline-4,6-dione hydrochloride by method D

(a)

4,4-Dimethyl-7-(2-methoxy-4-methylmercapto-benzoylamino)-8-nitro-2H,4H-isoquinoline-1,3-dione Prepared analogous to Example 2a from 5 gm of 4,4-dimethyl-7-amino-8-nitro-2H,4H-isoquinoline-1,3-dione and 2-methoxy-4-methylmercapto-benzoyl chloride.

Yield: 7.1 gm (82.6% of theory): M.p. above 270° C.

(b)

7,7-Dimethyl-2-(2-methoxy-4-methylmercapto-phenyl)-5H,7H-imidazo[4,5-h]isoquinoline-4,6-dione hydrochloride Prepared analogously to Example 1c from 7.1 gm of 4,4-dimethyl-7-(2-methoxy-4-methylmercapto-benzoylamino)-8-nitro-2H,4H-isoquinoline-1,3-dione. For purification, the obtained hydrochloride was converted into the free base, the base was chromatographed on a silicagel column (eluant: chloroform/acetone 19:1), and then the hydrochloride was precipitated from acetone by addition of ethereal hydrochlorice acid.

Yield: 5.6 gm (80% of theory); M.p. above 250° C.

EXAMPLE 4

7,7-Dimethyl-2-(2-methoxy-4-methylsulfinyl-phenyl)-5H,7H-imidazo[4,5-h]isoquinoline-4,6-dione 5.1 gm of 7,7-dimethyl-2-(2-methoxy-4-methylmercapto-phenyl)-5H,7H-imidazo[4,5-h]isoquinoline-4,6-dione were reacted in 100 ml of 70% acetic acid with 1.7 gm of 30% hydrogen peroxide, and the mixture was allowed to stand for 50 hours at room temperature (the first 3 hours while stirring). After 18 and again after 26 hours 1.3 gm of 30% hydrogen peroxide were added. The reaction mixture was then diluted with water, and ammonia was added until alkaline reaction. The precipitate was suction-filtered off and the filtrate was extracted twice with chloroform. The combined chloroform phases were evaporated, and the evaporation residue was combined with the precipitate. The thus obtained product was purified on a silicagel column (eluant: chloroform/acetone 19:1).

Yield: 3.5 gm (66% of theory); M.p. above 260° C.

EXAMPLE 5

7,7-Dimethyl-2-(2-methoxy-4-methylsulfonyl-phenyl)-5H,7H-imidazo[4,5-h]isoquinoline-4,6-dione 2.3 gm of 7,7-dimethyl-2-(2-methoxy-4-methylmercapto-phenyl)-5H,7H-imidazo[4,5-h]isoquinoline-4,6-dione were heated to 40° C. in 70 ml of 70% acetic acid, and a total of 10 ml of 30% hydrogen peroxide were added over a period of 10 hours. After standing overnight, the mixture was diluted with water, ammonia was added until alkaline reaction, and the mixture was saturated with sodium chloride and extracted several times with chloroform. The combined chloroform phases were evaporated, and the residue was purified on a silicagel column (eluant: chloroform/acetone 19:1).

Yield: 0.7 gm (28% of theory); M.p. above 250° C.

EXAMPLE 6

2,7,7-Trimethyl-5H,7H-imidazo[4,5-h]isoquinoline-4,6-dione hydrochloride

Prepared analogous to Example 1c from 16 gm of 4,4-dimethyl-7-acetamino-8-nitro-2H,4H-isoquinoline-1,3-dione.

Yield: 14.3 gm (93% of theory); M.p. above 260° C.

EXAMPLE 7

2-Ethyl-7,7-dimethyl-5H,7H-imidazo[4,5-h]isoquinoline-4,6-dione hydrochloride by method D

(a)

4,4-Dimethyl-7-propionylamino-8-nitro-2H,4H-isoquinoline-1,3-dione 29.1 gm of 4,4-dimethyl-7-acetamino-8-nitro-2H,4H-isoquinoline-1,3-dione were refluxed for 4 hours with 50 ml of propionic acid anhydride. The mixture was then poured into ice water and neutralized with sodium bicarbonate. The obtained precipitate was purified on a silicagel column (eluant: chloroform/acetone 19:1).

Yield: 21.8 gm (71.5% of theory); M.p. 238°–239° C.

(b)

2-Ethyl-7,7-dimethyl-5H,7H-imidazo[4,5-h]isoquinoline-4,6-dione hydrochloride Prepared analogously to Example 1c from 6.1 gm of 4,4-dimethyl-7-propionylamino-8-nitro-2H,4H-isoquinoline-1,3-dione.

Yield: 4.9 gm (83.5% of theory); M.p. 206°–207° C.

EXAMPLE 8

7,7-Dimethyl-2-(4-methylmercapto-phenyl)-5H,7H-imidazo[4,5h]isoquinoline-4,6-dione by method D

(a)

4,4-Dimethyl-7-(4-methylmercapto-benzoylamino)-8-nitro-2H,4H-isoquinoline-1,3-dione Prepared analogous to Example 1b from 14.6 gm of 4,4-dimethyl-7-acetamino-8-nitro-2H,4H-isoquinoline-1,3-dione and 17 gm of 4-methyl-mercapto-benzoyl chloride (reaction time: 23 hours).

Yield: 17 gm (85.1% of theory); M.p. over 265° C.

(b)

7,7-Dimethyl-2-(4-methylmercapto-phenyl)-5H,7H-imidazo[4,5-h]isoquinoline-4,6-dione 17. gm of 4,4-dimethyl-7-(4-methylmercapto-benzoylamino)-8-nitro-2H,4H-isoquinoline-1,3-dione were reduced analogous to Example 1c. After filtering off the catalyst, the mixture was evaporated to dryness, the remaining hydrochloride was converted with methanolic ammonia into the free base and then purified on a silicagel column (eluant: chloroform/acetone 19:1).

Yield: 5.8 gm (39% of theory); M.p. 251°–253° C.

EXAMPLE 9

7,7-Dimethyl-2-(4-methoxy-phenyl)-5H,7H-imidazo[4,5-h]isoquinoline-4,6-dione hydrochloride Prepared analogously to Example 1c from 80.5 gm of 4,4-dimethyl-7-(4-methoxy-benzoylamino)-8-nitro-2H,4H-isoquinoline-1,3-dione, where hydrogen chloride gas was introduced while refluxing.

Yield: 73.3 gm (93% of theory); M.p. 282° C.

EXAMPLE 10

7,7-Dimethyl-2-(4-hydroxy-phenyl)-5H,7H-imidazo[4,5-h]isoquinoline-4,6-dione (a)

7,7-Dimethyl-2(4-benzyloxy-phenyl)-5H,7H-imidazo[4,5-h]-isoquinoline-4,6-dione hydrochloride 1.5 gm of Raney nickel were added in portions over a period of 1 hour to a suspension of 8.3 gm of 4,4-dimethyl-7-(4-benzyloxy-benzoyl-amino)-8-nitro-2H,4H-isoquinoline-1,3-dione in a solution of 3 ml of hydrazine hydrate in 100 ml of ethanol, while stirring at room temperature. After another hour 100 ml of methanolic hydrochloric acid were added, and the mixture was slowly heated to its boiling point. After two hours of boiling, the reaction mixture was filtered, and the residue was extracted several times with boiling ethylene glycol monomethyl ether. The ethylene glycol monomethyl ether phases were combined with the methanolic filtrate and evaporated to 100 ml in vacuo. The precipitated product was suction-filtered off and recrystallized from water/ethanol.

Yield: 4 gm (44.7% of theory); M.p. 244°–246° C.

(b)

7,7-Dimethyl-2-(4-hydroxy-phenyl)-5H,7H-imidazo[4,5-h]isoquinoline-4,6-dione

A mixture consisting of 2.3 gm of 7,7-dimethyl-2-(4-benzyloxy-phenyl)-5H,7H-imidazo[4,5-h]isoquinoline-4,6-dione, 200 ml of methanol and 0.5 gm of 10% palladium-on-charcoal was hydrogenated at 50° C. at a hydrogen pressure of 5 atmospheres for 4 hours. The catalyst was then filtered off, the filtrate was evaporated to 50 ml and the precipitated crystals were suction-filtered off.

Yield: 1.5 gm (77.8% of theory); M.p. above 250° C.

EXAMPLE 11

7,7-Dimethyl-2-(2-methoxy-5-methylsulfonyl-phenyl)-5H,7H-imidazo[4,5-h]isoquinoline-4,6-dione (a)

4,4-Dimethyl-7-(2-methoxy-5-methylmercapto-benzoylamino)-8-nitro-2H,4H-isoquinoline-1,3-dione Prepared analogous to Example 1b (reaction time: 18 hours, the product was purified by boiling with n-propanol) from 29.1 gm of 4,4-dimethyl-7-acetamino-8-nitro-2H,4H-isoquinoline-1,3-dione and 30 gm of 2-methoxy-5-methylmercapto-benzoyl chloride.

Yield: 26.6 gm (61.9% of theory); M.p. above 255° C.

(b)

7,7-Dimethyl-2-(2-methoxy-5-methylmercapto-phenyl)-5H,7H-imidazo[4,5-h]isoquinoline-4,6-dione hydrochloride Prepared analogous to Example 1c from 25.7 gm of 4,4-dimethyl-7-(2-methoxy-5-methylmercapto-benzoylamino)-8-nitro-2H,4H-isoquinoline-1,3-dione.

Yield: 16.2 gm (64.6% of theory); M.p. sintering at 210° C.

(c)

7,7-Dimethyl-2-(2-methoxy-5-methylsulfonyl-phenyl)-5H,7H-imidazo[4,5-h]isoquinoline-4,6-dione A mixture consisting of 8.4 gm of 7,7-dimethyl-2-(2-methoxy-5-methylmercapto-phenyl)-5H,7H-imidazo[4,5-h]isoquinoline-4,6-dione, 200 ml of glacial acetic acid, 50 ml of water, 2 gm of sodium acetate and 10 ml of 30% hydrogen peroxide was heated at 50° C. for 10 days while stirring; after each two days another 5 ml of 30% hydrogen peroxide were added. The reaction mixture was poured over ice and neutralized with potassium carbonate. The precipitate was suction-filtered off and recrystallized from ethylene glycol monomethyl ether.

Yield: 2.7 gm (32.6% of theory); M.p. above 255° C.

EXAMPLE 12

7,7-Dimethyl-2-(4-chloro-phenyl)-5H,7H-imidazo[4,5-h]isoquinoline-4,6-dione hydrochloride Prepared analogous to Example 1c from 38.8 gm of 4,4-dimethyl-7-(4-chloro-benzoylamino)-8-nitro-2H,4H-isoquinoline-1,3-dione.

Yield: 22.5 gm (59.8% of theory); M.p. above 250° C. (from n-propanol).

EXAMPLE 13

7,7-Dimethyl-2-benzyl-5H,7H-imidazo[4,5-h]isoquinoline-4,6-dione

Prepared analogous to Example 1c from 29 gm of 4,4-dimethyl-7-phenyl-acetylamino-8-nitro-2H,4H-isoquinoline-1,3-dione. The base was liberated from the hydrochloride by addition of ammonia, purified on a silicagel column, and recrystallized from isopropanol.

Yield: 10 gm (39.7% of theory); M.p. 224°–225° C.

EXAMPLE 14

7,7-Dimethyl-2-phenylethyl-5H,7H-imidazo[4,5-h]isoquinoline-4,6-dione

Prepared analogous to Example 13 from 29.1 gm of 4,4-dimethyl-7-(3-phenyl-propionylamino)-8-nitro-2H,4H-isoquinoline-1,3-dione.

Yield: 6.3 gm (18.3% of theory); M.p. 241°–243° C.

EXAMPLE 15

7,7-Dimethyl-2-(2-methoxy-phenyl)-5H,7H-imidazo[4,5-h]isoquinoline-4,6-dione hydrochloride Prepared analogous to Example 1c from 37.3 gm of 4,4-dimethyl-7-(2-methoxy-benzoylamino)-8-nitro-2H,4H-isoquinoline-1,3-dione.

Yield: 12.2 gm (33.8% of theory); M.p. above 250° C. (from methanol).

EXAMPLE 16

7,7-Dimethyl-2-cyclohexyl-5H,7H-imidazo[4,5-h]isoquinoline-4,6-dione

Prepared analogously to Example 1c from 9.5 gm of 4,4-dimethyl-7-(cyclohexylcarbonyl-amino)-8-nitro-2H,4H-isoquinoline-1,3-dione. The hydrochloride was converted into the free base with ammonia and recrystallized from methanol.

Yield: 6.5 gm (79.3% of theory); M.p. 284° C. (decomp.).

EXAMPLE 17

7,7-Dimethyl-2-benzyl-5H,7H-imidazo[4,5-h]isoquinoline-4,6-dione by method A 9 gm of 2-benzyl-4-carboxy-5-(2-carboxy-2-propyl)-benzimidazole were dissolved in 80 ml of concentrated ammonia. The solution was evaporated to dryness, the residue was heated at 180° C. for one hour and the product was recrystallized from isopropanol.

Yield: 4.75 gm (56% of theory); M.p. 224°–225° C.

EXAMPLE 18

7,7-Dimethyl-2-cyclopropyl-5H-7H-imidazo[4,5-h]isoquinoline-4,6-dione hydrochloride (a)

4,4-Dimethyl-7-(cyclopropylcarbonyl-amino)-8-nitro-2H,4H-isoquinoline-1,3-dione Prepared analogous to Example 1b from 5.8 gm of 4,4-dimethyl-7-acetamino-8-nitro-2H,4H-isoquinoline-1,3-dione and 6.3 gm of cyclopropane carboxylic acid chloride (heating time: 30 hours).

Yield: 6 gm (94% of theory); (crude product, which was used without further purification).

(b)

7,7-Dimethyl-2-cyclopropyl-5H-7H-imidazo[4,5-h]isoquinoline-4,6-dione hydrochloride Prepared analogous to Example 1c from 6 gm of 4,4-dimethyl-7-(cyclopropylcarbonyl-amino)-8-nitro-2H,4H-isoquinoline-1,3-dione.

Yield: 4.8 gm (83% of theory); M.p. sintering at 208° C., decomp. at 240° C.

EXAMPLE 19

7,7-Dimethyl-2-(2-methoxy-5-methylsulfinyl-phenyl)-5H,7H-imidazo[4,5-h]isoquinoline-4,6-dione 3.0 gm of 7,7-dimethyl-2-(2-methoxy-5-metylmercapto-phenyl)-5H,7H-imidazo[4,5-h]isoquinoline-4,6-dione were dissolved in 60 ml of glacial acetic acid and then 0.88 ml of 30% hydrogen peroxide were slowly added dropwise at room temperature. After stirring for 30 minutes, the solution was neutralized with an aqueous saturated potassium carbonate solution, diluted with water and extracted with chloroform. The residual crude product obtained after evaporation of the chloroform was purified on a silicagel column (eluant: chloroform with increasing content of acetone).

Yield: 2.2 gm (74% of theory); M.p. sintering at 250° C.

EXAMPLE 20

2,7,7-Trimethyl-5-(3-diethylamino-propyl)-5H,7H-imidazo[4,5-h]-isoquinoline-4,6-dione dihydrochloride by method B 4.2 gm of 2,7,7-trimethyl-5H,7H-imidazo[4,5-h]isoquinoline-4,6-dione were dissolved in 50 ml of dimethylsulfoxide; the resulting solution was admixed in portions with 2.6 gm of a 55% suspension of sodium hydride in oil, and the mixture was stirred at room temperature for 2 hours. Then, 4.8 gm of 3-diethylamino-propyl bromide hydrobromide were added, and stirring was continued for one hour at room temperature and then for 4 hours at 80° C. After cooling, the mixture was diluted with water and extracted with chloroform. The chloroform phases were washed with water and evaporated, and the residue was purified on a silicagel column (eluent: chlorform/acetone 19:1). The dihydrochloride was precipitated from acetone/ethanol with ethereal hydrochloric acid.

Yield: 1.9 gm (29.5% of theory); M.p. above 250° C.

EXAMPLE 21

2,7,7-Trimethyl-5-(2-diethylamino-ethyl)-5H,7H-imidazo[4,5-h]isoquinoline-4,6-dione hydrochloride by method B 4.2 gm of 2,7,7-trimethyl-5H,7H-imidazo[4,5-h]isoquinoline-4,6-dione were dissolved in 100 ml of dimethylformamide, and the solution was admixed with 3.4 gm of diethylamino ethyl chloride hydrochloride and 4.1 gm of potassium carbonate. The mixture was refluxed for 8 hours, the solvent was distilled off in vacuo, the residue was admixed with water and extracted with chloroform. The chloroform phase was evaporated and the residue was purified on a silicagel column (eluant: chloroform/acetone 19:1). The dihydrochloride was precipitated from acetone/methanol with ethereal hydrochloric acid and recrystallized from acetone/methanol.

Yield: 1.2 gm (19.3% of theory); M.p. above 250° C.

EXAMPLE 22

7,7-Dimethyl-2-phenyl-5-(3-diethylamino-propyl)-5H,7H-imidazo[4,5-h]isoquinoline-4,6-dion dihydrochloride by method A A mixture consisting of 4.9 gm of 2-phenyl-4-carboxy-5-(2-carboxy-2-propyl)-benzimidazole, 2.6 gm of diethylaminopropyl-amine and 20 ml of ethylene glycol was heated at 180° C. for 1 hour. After cooling, the mixture was diluted with water and extracted twice with chloroform. The chloroform phases were evaporated, and the residue was purified on a silicagel column (eluant: chloroform/acetone 19:1). The dihydrochloride was precipitated from acetone with ethereal hydrochloric acid.

Yield: 5.6 gm (76% of theory): M.p. 205°–208° C.

EXAMPLE 23

7,7-Dimethyl-2-phenyl-5-(3-diethylamino-propyl)-5H,7H-imidazo[4,5-h]isoquinoline-4,6-dione dihydrochloride by method B 2.6 gm of a 55% suspension of sodium hydride in oil were added in portions to a mixture of 5.1 gm of 7,7-dimethyl-2-phenyl-5H,7H-imidazo[4,5-h]isoquinoline-4,6-dione hydrochloride and 50 ml of dimethyl sulfoxide. After stirring the mixture at room temperature for one hour, 4.8 gm of 3-diethylamino propyl bromide hdyrobromide were added, and the mixture was heated at 50° C. for 3 hours. The reaction mixture was admixed with water and extracted several times with chloroform. The chloroform phases were evaporated and the residue was purified on a silicagel column. The dihydrochloride was precipitated from acetone with ethereal hydrochloric acid and recrystallized from methanol/acetone.

Yield: 3.7 gm (50.5% of theory); M.p. 207°–209° C.

EXAMPLE 24

7,7-Dimethyl-2-phenyl-5-(2-diethylamino-ethyl)-5H,7H-imidazo[4,5-h]isoquinoline-4,6-dione dihydrochloride Prepared analogous to Example 23 from 5.1 gm of 7,7-dimethyl-2-phenyl-5H,7H-imidazo[4,5-h]isoquinoline-4,6-dione hydrochloride and 3.4 gm of 2-diethylamino-ethyl chloride hydrochloride, Yield: 3.8 gm (53.1% of theory); M.p. above 250° C.

EXAMPLE 25

7,7-Dimethyl-2-benzyl-5-(2-morpholino-ethyl)-5H,7H-imidazo[4,5-h]isoquinoline-4,6-dione dihydrochloride Prepared analogous to Example 23 from 1.6 gm of 7,7-dimethyl-2-benzyl-5H,7H-imidazo[4,5-h]isoquinoline-4,6-dione and 1.2 gm of 2-morpholino-ethyl chloride hydrochloride.

Yield: 0.5 gm (19.7% of theory); M.p. 243°–246° C.

EXAMPLE 26

7,7-Dimethyl-2-phenethyl-5-[2-(2-(3,4-dimethoxy-phenyl)-ethylamino)-ethyl]-5H,7H-imidazo[4,5-h]-isoquinoline-4,6-dione dihydrochloride by method C (a)

7,7-Dimethyl-2-phenethyl-5-(2-chloro-ethyl)-5H,7H-imidazo-[4,5-h]isoquinoline-4,6-dione Prepared analogous to Example 23 at room temperature from 4.3 gm of 7,7-dimethyl-2-phenethyl-5H,7H-imidazo[4,5-h]isoquinoline-4,6-dione and 2.2 gm of 2-bromo-1-chloro-ethane. The viscous oily crude product was directly further processed.

Yield: 5.3 gm (100% of theory).

(b)

7,7-Dimethyl-2-phenethyl-5-[2-(2-(3,4-dimethoxy-phenyl)ethylamino)-ethyl]-5H,7H-imidazo[4,5-h]isoquinoline-4,6-dione dihydrochloride 2.8 gm of 7,7-dimethyl-2-phenethyl-5-(2-chloro-ethyl)-5H,7H-imidazo[4,5-h]isoquinoline-4,6-dione were heated at 150° C. for 40 minutes with 5 ml of 2-(3,4-dimethoxy-phenyl)-ethylamine. After cooling, the mixture was dissolved in ether, and the solution was several times extracted with water weakly acidified with acetic acid. The organic phase was evaporated, and the residue was dissolved in acetone. The dihycrochloride was precipitated from the acetone solution with ethereal hydrochloric acid.

Yield: 0.8 gm (18.4% of theory); M.p. 207°–210° C. (decomp.).

EXAMPLE 27

7,7-Dimethyl-2-phenyl-5-(3-piperidino-propyl)-5H,7H-imidazo[4,5-h]isoquinoline-4,6-dione dihydrochloride Prepared analogous to Example 23 from 3.4 gm of 7,7-dimethyl-2-phenyl-5H,7H-imidazo[4,5-n]isoquinoline-4,6-dione hydrochloride and 3.4 gm of 3-piperidino-propyl chloride.

Yield: 3.2 gm (63.6% of theory); M.p. 234°–238° C. (sintering at 227° C.).

EXAMPLE 28

7,7-Dimethyl-2-(2-methoxy-phenyl)-5-[3-(2-(3,4-dimethoxyphenyl)-ethylamino)-propyl]-5H,7H-imidazo[4,5-h]isoquinoline-4,6-dione dihydrochloride by method C (a)

7,7-Dimethyl-2-(2-methoxy-phenyl)-5-(3-chloro-1-propyl)-5H,7H-imidzao[4,5-h]isoquinoline-4,6-dione Prepared analogous to Example 23 from 3.7 gm of 7.7-dimethyl-2-(2-methoxy-phenyl)-5H,7H-imidazo[4,5-h]isoquinoline-4,6-dione hydrochloride and 1.9 gm of 1-bromo-3-chloro propane. The product precipitated by addition of water to the reaction solution was dissolved in methylene chloride, the solution was dried, and after evaporation of the methylene chloride the residue was recrystallized from isopropanol.

Yield: 3.5 gm (85% of theory); M.p. 154°–156° C.

(b)

7,7-Dimethyl-2-(2-methoxy-phenyl)-5-[3-(2-(3,4-dimethoxy-phenyl)-ethylamino)-propyl]-5H,7H-imidazo[4,5-h]isoquinoline-4,6-dione dihydrochloride 3.4 gm of 7,7-dimethyl-2-(2-methoxy-phenyl)-5-(3-chloro-1-propyl)-5H,7H-imidazo[4,5-h]isoquinoline-4,6-dione were heated at 140° C. for 30 minutes with 4.2 gm of 2-(3,4-dimethoxy-phenyl)-ethylamine. The reaction mixture was separated by column chromatography on silicagel (eluant: chloroform/acetone 19:1). The desired product was dissolved in acetone. The dihydrochloride was precipitated with ethereal hydrochloric acid and recrystallized from isopropanol.

Yield: 3.7 gm (71.7% of theory); M.p. 192°–194° C. (decomp.).

EXAMPLE 29

7,7-Dimethyl-2-cyclohexyl-5-(3-di-n-propylamino-propyl)-5H,7H-imidazo[4,5-h]isoquinoline-4,6-dione dihydrochloride by method C (a)

7,7-Dimethyl-2-cyclohexyl-5-(3-chloro-propyl)-5H,7H-imidazo-[4,5-h]isoquinoline-4,6-dione Prepared analogous to Example 26a from 3.1 gm of 7,7-dimethyl-2-cyclohexyl-5H,7H-imidazo[4,5-h]isoquinoline-4,6-dione and 1.9 gm of 1-bromo-3-chloro-propane. The crude product was directly further processed.

(b)

7,7-Dimethyl-2-cyclohexyl-5-(3-di-n-propylamino-propyl)-5H,7H-imidazo[4,5-h]isoquinoline-4,6-dione dihydrochloride The crude product obtained in step (a) was refluxed with 15 ml of di-n-propylamine for 5 hours. The excess amine was distilled off in vacuo, the residue was admixed with water, and the aqueous mixture was extracted with methylene chloride. The combined organic phaes were evaporated and the residue was purified on a silicagel column (eluant: chloroform/acetone 19:1). The dihydrochloride was precipitated from acetone with etereal hydrochloric acid (very slow crystallization), suction-filtered off, and washed with acetone/ether.

Yield: 1.1 gm (21% of theory, based on 7,7-dimethyl-2-cyclohexyl-5H-7H-imidazo[4,5-h]isoquinoline-4,6-dione); M.p. 156°–158° C.

EXAMPLE 30

7,7-Dimethyl-2-benzyl-5-(3-diethylamino-propyl)-5H,7H-imidazo[4,5-h]isoquinoline-4,6-dione-dihydrochloride Prepared abalogous to Example 23 from 3.2 gm of 7,7-dimethyl-2-benzyl-5H,7H-imidazo[4,5-h]isoquinoline-4,6-dione and 3,4 gm of diethylaminopropyl bromide hydrobromide.

Yield: 1.3 gm (25.8% of theory); M.p. 150°–153° C. (sintering at 130° C.; from acetone).

EXAMPLE 31

7,7-Dimethyl-2-(4-chloro-phenyl)-5-[2-(N-methyl-N-(2-(3,4-dimethoxy-phenyl)-ethyl)-amino)-ethyl]-5H,7H-imidazo[4,5-h]isoquinoline-4,6-dione dihydrochloride by method C (a)

7,7-Dimethyl-2-(4-chloro-phenyl)-5-(2-chloro-ethyl)-5H,7H-imidazo[4,5-h]isoquinoline-4,6-dione Prepared analogous to Example 23 from 7.5 gm of 7,7-dimethyl-2-(4-chloro phenyl)-5H,7H-imidazo[4,5-h]isoquinoline-4,6-dione and 6.9 gm of 1-bromo-2-chloro-ethane.

Yield: 4.2 gm (50.7% of theory); M.p. 176°–177° C.

(b)

7,7-Dimethyl-2-(4-chloro-phenyl)-5-[2-(N-methyl-N-(2-(3,4-dimethoxy-phenyl)-ethyl)-amino)-ethyl]-5H,7H-imidazo[4,5-h]-isoquinoline-4,6-dione dihydrochloride A mixture consisting of 1.5 gm of 7,7-dimethyl-2-(4-chlorophenyl)-5-(2-chloro-ethyl)-5H,7H-imidazo[4,5-h]isoquinoline-4,6-dione and 1.7 gm of N-methyl-N-(2-(3,4-dimethoxy-phenyl)-ethyl)-amine was heated at 150° C. for 3 hours. After cooling the reaction mixture was dissolved in chloroform, and the solution was washed with water. The chloroform phase was evaporated, and the residue was chromatographed on a silica-gel column (eluant: chloroform/acetone 19:1). The dihydrochloride was precipitated from acetone by addition of ethereal hydrochloric acid and recrystallized from methylene chloride/acetone.

Yield: 0.8 gm (35% of theory); M.p. 230°–231° C. (decomp.).

EXAMPLE 32

7,7-Dimethyl-2-(4-chloro-phenyl)-5-(3-diethylamino-propyl)-5H,7H-imidazo[4,5-h]isoquinoline-4,6-dione dihydrochloride Prepared analogous to Example 23 from 3.8 gm of 7,7-dimethyl-2-(4-chloro-phenyl)-5H,7H-imidazo[4,5-h]isoquinoline-4,6-dione and 3.1 gm of 3-diethylamino-propyl bromide hydrobromide.

Yield: 1.5 gm (28.5% of theory); M.p. 206°–208° C.

EXAMPLE 33

7,7-Dimethyl-2-(4-chloro-phenyl)-5-[2-(4-methyl-1-piperazinyl)-ethyl]-5H,7H-imidazo[4,5-h]isoquinoline-4,6-dione trihydrochloride by method C A mixture consisting of 2.1 gm of 7,7-dimethyl-2-(4-chloro-phenyl)-5-(2-chloro-ethyl)-5H,7h-imidazo[4,5-h]isoquinoline-4,6-dione and the 10 ml of N-methyl-piperazine was heated at 130° C. for 2 hours. After distilling off the excess of N-methyl-piperazine in vacuo, the residue was purified on a silicagel column (eluant: chloroform/acetone 19:1). The trihydrochloride was precipitated from acetone by addition of ethereal hydrochloric acid and recrystallized from ethanol.

Yield: 1 gm (34.7% of theory); M.p. 263°–266° C. (decomp.)

EXAMPLE 34

7,7-Dimethyl-2-(2-methoxy-4-methylmercapto-phenyl)-5-(2-diethylamino-ethyl)-5H,7H-imidazo[4,5-h]isoquinoline-4,6-dione dihydrochoride Prepared analogously to Example 23 from 2.9 gm of 7,7-dimethyl-2-(2-methoxy-4-methylmercapto-phenyl)-5H,7H-imidazo[4,5-h]isoquinoline-4,6-dione hydrochloride and 2 gm of 2-diethylamino-ethyl bromide hydrobromide.

Yield: 1.3 gm (33.5% of theory); M.p. 235°–238° C.

EXAMPLE 35

7,7-Dimethyl-2-(4-methoxy-phenyl)-5-[2-(2-(3,4-dimethoxy phenyl)-ethylamino)-ethyl]-5H,7H-imidazo[4,5-h]isoquinoline-4,6-dione dihydrochloride Prepared analogous to Example 26b from 1 gm of 7,7-dimethyl-2-(4-methoxy-phenyl)-5-(2-chloro-ethyl)-5H,7H-imidazo[4,5-h]isoquinoline-4,6-dione and 3 gm of 2-(3,4-dimethoxyphenyl)-ethyl-amine.

Yield: 0.3 gm (19.5% of theory); M.p. 210°–212° C. (from isopropanol)

EXAMPLE 36

7,7-Dimethyl-2-phenethyl-5-(2-methylamino-ethyl)-5H,7H-imidazo-[4,5-h]isoquinoline-4,6-dione-dihydrochloride by method A A mixture consisting of 3.0 gm of 2-phenylethyl-4-carboxy-5-(2-carboxy-2-propyl)-benzimidazole, 2 ml of methylamino-ethylamine and 15 ml of ethylene glycol was heated at 180° C. for 2 hours. After distilling off the ethylene glycol in vacuo, the mixture was dissolved in chloroform, and the solution was washed with an aqueous sodium chloride solution. After distilling off the chloroform, the residue was dissolved in acetone, and the dihydrochloride was precipitated by addition of methanolic hydrochloric acid.

Yield: 3.2 gm (81.2% of theory); M.p. 181°–184° C.

EXAMPLE 37

7,7-Dimethyl-2-(4-methoxy-phenyl)-5-)2-methylamino-ethyl)-5H,7H-imidazo[4,5-h]isoquinoline-4,6,dione dihydrochloride Prepared analogous to Example 36 from 3 gm of 2-(4-methoxyphenyl)-4-carboxy-5-(2-carboxy-2-propyl)-benzimidazole and 2 ml of methylaminoethyl-amine. Before precipitating the dihydrochloride the base was chromatographed on a silicagel column (eluant: chloroform/acetone 19:1).

Yield: 1.1 gm (23.6% of theory); M.p. above 260° C.

EXAMPLE 38

7,7-Dimethyl-2-phenyl-5-[3-(4-methyl-1-piperazinyl)-propyl]-5H-7H-imidazo[4,5-h]isoquinoline-4,6-dione trihydrochloride Prepared analogous to Example 36 from 1.6 gm of 2-phenyl-4-carboxy-5-(2-carboxy-2-propyl)-benzimidazole and 0.94 gm of 3-(4-methyl-1-piperazinyl)-propylamine.

Yield: 2.5 gm (90% of theory); M.p. 235° C. (decomp.)

EXAMPLE 39

7,7-Dimethyl-2-phenyl-5-(2-dimethylamino-ethyl)-5H,7H-imidazo[4,5-h]isoquinoline-4,6-dione dihydrochloride Prepared analogous to Example 36 from 1.6 gm of 2-phenyl-4-carboxy-5-(2-carboxy-2-propyl)-benzimidazole and 0.53 gm of 2-dimethylamino-ethylamine.

Yield: 1.5 gm (66.8% of theory); M.p. 234°–237° C.

EXAMPLE 40

7,7-Dimethyl-2-phenyl-5-(2-morpholino-ethyl)-5H,7H-imidazo[4,5-h]isoquinoline-4,6-dione hydrochloride Prepared analogous to Example 36 from 1.6 gm of 2-phenyl-4-carboxy-5-(2-carboxy-2-propyl)-benzimidazole and 0.78 gm of 2-morpholino-ethylamine.

Yield: 2 gm (81.4% of theory): M.p. 261°–263° C.

EXAMPLE 41

7,7-Dimethyl-2-phenyl-5-(3-dimethylamino-propyl)-5H,7H-imidazo[4,5-h]isoquinoline-4,6-dione dihydrochloride Prepared analogous to Example 23 from 3.4 gm of 7,7-dimethyl-2-phenyl-5H,7H-imidazo( 4,5-h]isoquinoline-4,6-dione hydrochloride and 1.7gm of 3-dimethylamino-propyl chloride hydrochloride (reaction temperature: 50°–60° C.; reaction time: 18 hous).

Yield: 1.5 gm (32.4% of theory); M.p. 234°–235° C.

EXAMPLE 42

7,7-Dimethyl-2-cyclopropyl-5-(3-diethylamino-propyl)-5H,7H-imidazo[4,5-h]isoquinoline-4,6-dione Prepared analogous to Example 23 from 2.45 gm of 7,7-dimethyl-2-cyclopropyl-5H,7H-imidazo[4,5-h]isoquinoline-4,6-dione hydrochloride and 2.3 gm of 3-diethylamino-propyl bromide hydrobromide. The crude product was purified by chromatography on a silicagel column (eluant: chloroform with increasing content of acetone).

Yield: 1.3 gm (36% of theory); M.p. 185°–187° C. (decomp.).

EXAMPLE 43

2,7,7-Trimethyl-5-[3-(2-(3,4-dimethoxy-phenyl)-ethylamino)-propyl]-5H,7H-imidkazo[4,5-h]isoquinoline-4,6-dione difumerate Prepared analogous to Example 22, but without a solvent, from 3.4 gm of 2-methyl-4-carboxy-5-(2-carboxy-2-propyl)-benzimidazole and 3.4 gm of 3-[2-(3,4-dimethoxy-phenyl)-ethylamino]-propylamine. The difumarate was precipitated from acetone.

Yield: 5.5 gm (61% of theory); M.p. 134°–135° C. (decomp.).

EXAMPLE 44

7,7-Dimethyl-2-phenyl-5-(3-diethylamino-propyl)-5H,7H-imidazo[4,5-h]isoquinoline-4,6-dione dihydrochloride by method A A mixture consisting of 1.06 gm of 5,7,7-trimethyl-2-phenyl-5H,7H-imidazo[4,5-h]isoquinoline-4,6-dione and 3 ml of 3-diethylamino-propyl-amine was heated at 170° C. for 30 hours. After distilling off the excess amine in vacuo, the residue was admixed with water and further processed analogous to Example 22.

Yield: 0.29 gm (20% of theory); M.p. 205°–208° C.

EXAMPLE 45

7,7-Dimethyl-2-phenyl-5-(3-ethylamino-propyl)-5H,7H-imidazo[4,5-h]isoquinoline-4,6-dione-dihydrochloride Prepared analogously to Example 22, but without a solvent and at 130° C., from 3,2 g of 2-phenyl-4-carboxy-5-(2-carboxy-2-propyl)-benzimidazole and 3 ml of 3-ethyl-aminopropylamine. The dihydrochloride was precipitated from acetone with methanolic hydrochloric acid.

Yield: 3,6 gm (77.7% of theory); M.p. 226°–230° C.

The compounds of the present invention, that is, those embraced by formula I and their non-toxic, pharmacologically acceptable acid addition salts, have useful properties. More particularly, they exhibit cardiovascular and anxiolytic (anxiety-relieving) activities in warm blooded animals, such as cats and mice. Thus the compounds of the formula I wherein A is hydrogen and their non-toxic acid addition salts exhibit cardiotonic, hypotensive and platelet aggregation inhibiting activities, and those wherein A is $-(CH_2)_n-NR_2R_3$ and their non-toxic acid addition salts exhibit antiarrhythmic activity. In addition, those compounds of the formula I wherein A is hydrogen are useful as intermediates for the preparation of 5-aminoalkyl-substituted imidazoisoquinoline-4,6-diones.

The above-indicated pharmacological properties of the compounds of this invention were ascertained by the test methods described below, and Tables I–IV show the results obtained from these tests for a few representative species of the genus, where A = 7,7-Dimethyl-2-(2,4-dimethoxy-phenyl)-5H,7H-imidazo[4,5-h]isoquinoline-4,6-dione hydrochloride,
B = 7,7-Dimethyl-2-(2-methoxy-4-methylsulfonyl-phenyl)-5H,7H-imidazo[4,5-h]isoquinoline-4,6-dione,
C = 7,7-Dimethyl-2-phenylethyl-5H,7H-imidazo[4,5-hisoquinoline-4,6-dione,
D = 7,7-Dimethyl-2-benzyl-5H,7H-imidazo[4,5-h]isoquinoline-4,6-dione,
E = 7,7-Dimethyl-2-(2-methoxy-phenyl)-5H,7H-imidazo[4,5-h]isoquinoline-4,6-dione hydrochloride,
F = 7,7-Dimethyl-2-cyclohexyl-5H,7H-imidazo[4,5-h]isoquinoline-4,6-dione,
G = 7,7-Dimethyl-2-(4-chloro-phenyl)-5H,7H-imidazo[4,5-h]isoquinoline-4,6-dione hydrochloride,
H = 7,7-Dimethyl-2-(4-methylmercapto-phenyl)-5H,7H-imidazo[4,5-h]isoquinoline-4,6-dione,
I = 7,7-Dimethyl-2-(4-methoxy-phenyl)-5H,7H-imidazo[4,5-h]isoquinoline-4,6-dione hydrochloride,
J = 7,7-Dimethyl-2-(4-hydroxy-phenyl)-5H,7H-imidazo[4,5-h]isoquinoline-4,6-dione hydrochloride,
K = 7,7-Dimethyl-2-(2-methoxy-5-methylsulfonyl-phenyl)-5H,7H-imidazo[4,5-h]isoquinoline-4,6-dione,
L = 7,7-Dimethyl-2-(2-methoxy-5-methylsulfinyl-phenyl)-5H,7H-imidazo[4,6-h]isoquinoline-4,6-dione hydrochloride,
M = 7,7-Dimethyl-2-cyclopropyl-5H,7H-imidazo[4,5-h]isoquinoline-4,6-dione hydrochloride,
N = 7,7-Dimethyl-2-phenyl-5-(2-diethylamino-ethyl)-5H,7H-imidazo[4,5-h]isoquinoline-4,6-dione dihydrochloride,
O = 7,7-Dimethyl-2-phenyl-5-(3-diethylamino-propyl)-5H,7H-imidazo[4,5-h]isoquinoline-4,6-dione dihydrochloride,
P = 7,7-Dimethyl-2-phenyl-5-(3-piperidino-propyl)-5H,7H-imidazo[4,5-h]isoquinoline-4,6-dione dihydrochloride, and
Q = 7,7-Dimethyl-2-phenyl-5-(2-dimethylamino-ethyl)-5H,7H-imidazo[4,5-h]isoquinoline-4,6-dione-dihydrochloride.

1. Cardiotonic and blood pressure effects

Cats of both sexes with a body weight of 2 to 4 kg were anesthetized by intraperitoneal injection of 30 mgm/kg of sodium pentobarbital. The arterial blood pressure was measured by a Statham pressure transducer (P23 Dc) from the aorta abdominalis via a PVA-Catheter, which was inserted through the right arteria femoralis. The ventricle pressure was measured by a cathetertip manometer (type MILLAR PC-350), which was introduced into the left ventricle via the right arteria carotis. The indices of contractility dp/dt max. were obtained by a differentiating amplifier. The arterial blood pressure and dp/dt max. were continuously recorded by direct-writer. The test compounds were injected intravenously at 2 mg/kg.

The following table shows the results:

Table I

| Compound | Change in blood pressure mm Hg | Increase in dp/dt % | Duration min. |
|---|---|---|---|
| A | −49/−48 | + 83 | > 24 |
| B | −52/−80 | + 76 | > 56 |
| C | −40/−50 | + 87 | > 20 |
| D | −67/−63 | +110 | > 57 |
| E | −46/−63 | + 77 | 12 |
| F | −23/−40 | + 86 | > 42 |
| G | −40/−30 | + 45 | 9 |
| H | −45/−45 | + 46 | > 12 |
| I | −33/−46 | + 32 | > 19 |
| J | −47/−58 | + 62 | > 29 |
| K | −70/−67 | +157 | >107 |
| L | −42/−53 | + 90 | > 70 |
| M | −41/−49 | +108 | > 55 |

2. Effect on the effective refractory period of the isolated electrically stimulated left auricle of the guinea pig Method Guinea pigs of both sexes were killed by a blow on the neck. After opening the thorax, the heart was quickly removed and transferred into a Tyrode's solution (37° C.). The auricles were separated from the ventricles along the Annulus fibrosus, and only the left auricles were used. Electrical stimulation was performed by a Grass stimulator, S4G, with square wave impulses of 1 millisecond duration and a stimulation voltage of 12 V. The auricles were suspended in Tyrode's solution at 37° C. containing 136.8 mVal NaCl, 2.68 mVal KCL, 0.2625 mVal $MgCl_2$, 0.417 mVal $NaH_2PO_4$, 11.9 mVal $NaHCO_3$, 1.8 mVal CaCl, and 3 gm of glucose perliter. The solution was continuously aerated with $O_2/CO_2$ (98%/2%). The isometric contractions were measured with a force displacement transducer and recorded on a Grass polygraph (P5). The number of the contractions was counted out and compared with the frequency indicated at the stimulator.

The maximum stimulation frequency was determined by increasing the stimulation rate every 10 seconds by 1 Hz. The maximum stimulation frequency was measured in preliminary tests by determining the average value. During the intervals of 5 minutes each between the measurements, the stimulation rate was 0.5 Hz.

After the determination of the average value the test compound was added to the Tyrode's solution and the stimulation rate was maintained at 0.5 Hz. During the first 5 minutes the inotropic effect of the compound was observed. Measurements were performed every 5 and 10 minutes after addition of the test compound. The average value resulting from the two tests (value at 5 minutes and 10 minutes, respectively) was taken as the maximum stimulation frequency after addition of the test compound. At first small doses were given, and after determination of the maximum stimulation frequency the dose was increased cumulatively and the maximum stimulation frequency for that dose was measured.

Principle

The maximum stimulation frequency is measured by increasing the stimulation rate. When the interval between two stimuli is shortened, a stimulation rate is reached at which every second stimulation falls into the refractory period of the foregoing contraction and will not be answered with a contraction. So, the maximum stimulation frequency is a measure of the effective refractory period. Compounds which reduce the maximum stimulation frequency, prolong the refractory period.

From the dose response curves the concentrations which reduce the maximum stimulation frequency by 50%, were graphically determined:

Table II

| Compound | $EC_{50}$ in μgm/ml |
|---|---|
| N | 1.8 |
| O | 5.0 |
| P | 6.7 |
| Q | 4.8 |

3. Antiarrhythmic effect against chloroform-induced ventricular fibrillation in mice On placing a mouse into a chloroform-saturated atmosphere, the animal becomes anesthetized after 40 sec., the spontaneous respiration stops, and after 20 sec. more, gasping respiration sets in.

Immediately after the gasping respiration has ceased, the mouse is taken out of the chloroform atmosphere, the thorax is opened, and the heart is quickly exposed to allow inspection of the heart movement. For 1 minute after opening the thorax, spontaneous ventricular fibrillation occurs in nearly all the animals or can be induced by touching the heart with tweezers.

Pre-treatment with antiarrhythmic compounds reduces the number of animals which show fibrillation in a dose-dependent way. The dose which reduces the number of animals having fibrillations by 50% ($ED_{50}$) is calculated by means of dose-response curves and the standard deviation is determined [MILLER, L. C. and TAINTER, M. L., Proc. Soc. Exp. Biol. Med. 57, 261 (1944)].

The tests were performed on male mice, body weight 20–25 gm. Each dose was tested on 10 animals.

The dose was determined, at which after i.v. and p.o. administration one minute before starting the test, the ventricular fibrillation was prevented in 50% of the animals.

Table III

| Compound | $ED_{50}$ i.v. | mg/kg p.o. | oral activity $ED_{50}$ i.v. × 100/$ED_{50}$ p.o. |
|---|---|---|---|
| N | 2.4 | 21.2 | 11.1% |
| O | 6.4 | 29 | 22.1% |
| P | 10.5 | 130 | 8.1% |
| Q | 6.1 | 23.5 | 26.0% |

4. Acute Toxicity

The acute toxicity was determined in mice after oral or intravenous administration. The dose was determined at which 50% of the animals died:

Table IV

| Compound | Toxicity |
|---|---|
| D | >300 mgm/kg p.o. |
| F | >300 mgm/kg p.o. |
| K | >300 mgm/kg p.o. |
| O | $LD_{50}$: 92 mgm/kg p.o. |
|   | 61 mgm/kg i.p. |

The above pharmacological data indicate that those compounds of the formula I wherein A is hydrogen are useful for the treatment of cardiac insufficiency and hypertension, and that those wherein A is other than hydrogen are useful for the treatment of cardiac arrhythmia, especially in conjunction with myocardial infarction and angino pectoris.

For pharmaceutical purposes the compounds of the present invention are administered to warm-blooded animals peorally, parenterally or rectally as active ingredients in customary dosage unit compositions, that is, compositions in dosage unit form consisting essentially of an inert pharmaceutical carrier and one effective dosage of the active ingredient, such as tables, coated pills, capsules, wafers, powders, solutions, suspensions, emulsions, syrups, suppositories and the like. One effective dosage unit of the compounds according to the present invention is from 0.83 to 5.0 mgm/kg body weight for those where A is hydrogen, and from 0.33 to 0.83 mgm/kg body weight for those where A is other than hydrogen.

The following examples illustrate a few pharmaceutical dosage unit compositions comprising a compound of the present invention as an activie ingredient and represent the best modes contemplated of putting the invention into practice use. The parts are parts by weight unless otherwise specified.

EXAMPLE 45

Tablets

The tablet composition is compounded from the following ingredients:

| | |
|---|---|
| 7,7-Dimethyl-2-phenyl-5-(3-diethylamino-propyl)-5H,7H-imidazo[4,5-h]isoquinoline-4,6-dione dihydrochloride | 50.0 parts |
| Lactose | 100.0 parts |
| Polyvinylpyrrolidone | 5.0 parts |
| Carboxymethyl cellulose | 19.0 parts |
| Magnesium stearate | 1.0 parts |
| | Total 175.0 parts |

Preparation

The active ingredient is intimately admixed with the lactose and the polyvinylpyrrolidone, the mixture is granulated by moist screening through a 1.5 mm-mesh screen, the granulate is dried at 50° C. in a circulating air dryer, and the dry granulate is again passed through a 1.0 mm-mesh screen. The magnesium stearate and the carboxymethyl cellulose are then blended into the granulate, and the resulting composition is compressed into 175 mgm-tablets. Each tablet is an oral dosage unit composition containing 50 mgm of the active ingredient.

EXAMPLE 46

Coated Pills

The pill core composition is compounded from the following ingredients.

| | |
|---|---|
| 7,7-Dimethyl-2-phenyl-5-(3-diethylamino-propyl)-5H,7H-imidazo[4,5-h]isoquinoline-4,6-dione hydrochloride | 25.0 parts |
| Corn starch, dried | 45.0 parts |
| Soluble starch | 2.0 parts |
| Carboxymethyl cellulose | 7.0 parts |
| Magnesium stearate | 1.0 parts |
| | Total 80.0 parts |

Preparation

The active ingredient and the corn starch are intimately admixed with each other, the mixture is moistened with an aqueous solution of the soluble starch and granulated through a 1.0 mm-mesh screen, the granulate is dried at 50° C. in a circulating air dryer, and the dry granulate is again passed through the above screen. The carboxymethyl cellulose and the magnesium stearate are then blended into the granulate, and the resulting composition is compressed into 80 mgm-pill cores which are subsequently coated with a thin shell consisting essentially of sugar and talcum. Each coated pill is an oral dosage unit composition containing 25 mgm of the active ingredient.

EXAMPLE 47

Suppositories

The suppository composition is compounded from the following ingredients:

| | |
|---|---|
| 7,7-Dimethyl-2-phenyl-5-(3-diethylamino-propyl)-5H,7H-imidazo[4,5-h]isoquinoline-4,6-dione hydrochloride | 50.0 parts |
| Suppository base (e.g. cocoa butter) | 1650.0 parts |
| | Total 1700.0 parts |

Preparation

The suppository base is melted, cooled to 38° C., and the pulverized active ingredient is homogeneously dispersed therein. The composition is then cooled to 35° C., and 1700 mgm-portions thereof are poured into cooled suppository molds and allowed to harden therein. Each suppository is a rectal dosage unit composition containing 50 mgm of the active ingredient.

EXAMPLE 48

Hypodermic Solution

The solution is compounded from the following ingredients:

| | |
|---|---|
| 7,7-Dimethyl-2-phenyl-5-(3-diethylamino-propyl)-5H,7H-imidazo[4,5-h]isoquinoline-4,6-dione dihydrochloride | 50.0 parts |
| Sorbitol | 250.0 parts |

| | |
|---|---|
| -continued | |
| Distilled water q.s. ad. | 5000.0 parts by vol. |

Preparation

The active ingredient and the sorbitol are dissolved in a sufficient amount of distilled water, and the solution is diluted to the indicated volume with additional distilled water and then filtered until free from suspended particles. The filtrate is filled into 5 cc-ampules which are then sterilized for 20 minutes at 120° C. and sealed. Each ampules contains 50 mgm of the active ingredient, and its contents are an injectable dosage unit composition.

EXAMPLE 49

Drop Solution

The solution is compounded from the following ingredients:

| | |
|---|---|
| 7,7-Dimethyl-2-phenyl-5-(3-diethylamino-propyl)-5H,7H-imidazo[4,5-h]isoquinoline-4,6-dione dihydrochloride | 5.0 parts |
| Methyl p-hydroxybenzoate | 0.034 parts |
| Propyl p-hydroxybenzoate | 0.015 parts |
| Anise oil | 0.05 parts |
| Menthol | 0.06 parts |
| Saccharin sodium | 1.0 parts |
| Glycerin | 10.0 parts |
| Ethanol | 40.0 parts |
| Distilled water q.s.ad | 100.0 parts by vol. |

Preparation

The p-hydroxy-benzoates are dissolved in the ethanol and the anise oil and the menthol are added thereto (solution I). The active ingredient, the glycerin and the saccharin sodium are dissolved in the distilled water (solution II). Solution II is added to solution I, and the mixed solution is filtered until clear. 5 ml of the filtrate are an oral dosage unit composition containing 25 mgm of the active ingredient.

Any one of the other compounds embraced by formula I or a non-toxic pharmaceutically acceptable acid addition salt thereof may be substituted for the particular active ingredient in Examples 45 through 49. Likewise, the amount of active ingredient in these illustrative examples may be varied to achiev the dosage unit ranges set forth above, and the amounts and nature of the inert pharmaceutical carrier ingredient may be varied to meet particular requirements.

While the present invention has been illustrated with the aid of certain specific embodiments thereof, it will be readily apparent to others skilled in the art that the invention is not limited to these particular embodiments, and that various changes and modifications may be made without departing from the spirit of the invention or the scope of the appended claims.

We claim:

1. A compound of the formula

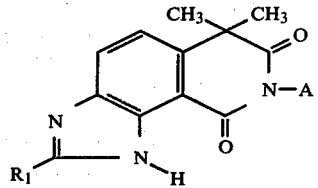

wherein
$R_1$ is lower alkyl of 1 to 6 carbon atoms; phenyl-lower alkyl; cycloalkyl of 3 to 6 carbon atoms; phenyl; or mono- or di-substituted phenyl, where the substituents are each halogen, hydroxyl or methoxy, or one of them is methyl-mercapto, methylsulfinyl, methylsulfonyl or benzyloxy or both are identical methyl-mercapto, methylsulfinyl, methylsulfonyl or benzyloxy groups; and
A is hydrogen or

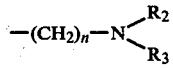

where
$R_2$ is hydrogen or lower alkyl;
$R_3$ is lower alkyl of 1 to 6 carbon atoms or dimethoxyphenyl-lower alkyl; or
$R_2$ and $R_3$, together with each other and the nitrogen atom to which they are attached, are piperidino, morpholino or N'-lower alkyl-piperazino; and
n is 2 or 3;
or a non-toxic, pharmacologically acceptable acid addition salt thereof.

2. A compound of claim 1, where
$R_1$ is lower alkyl; phenyl-lower alkyl; cycloalkyl of 3 to 6 carbon atoms; phenyl; or mono- or di-substituted phenyl, where the substituents are each fluorine, chlorine, bromine or methoxy, or one of them is methylmercapto, or both are identical methylmercapto groups; and
A is

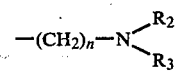

where
$R_2$ is hydrogen or lower alkyl;
$R_3$ is lower alkyl or dimethoxyphenyl-lower alkyl; or
$R_2$ and $R_3$, together with each other and the nitrogen atom to which they are attached, are piperidino, morpholino or N'-lower alkyl-piperazino; and
n is 2 or 3;
or a non-toxic, pharmacologically acceptable acid addition salt thereof.

3. A compound of claim 1, where
$R_1$ is lower alkyl of 1 to 6 carbon atoms; phenyl-lower alkyl; cycloalkyl of 3 to 6 carbon atoms, phenyl; or mono- or di-substituted phenyl, where the substituents are each halogen, hydroxyl or methoxy, or one of them is methylmercapto, methylsulfinyl, methylsulfonyl or benzyloxy, or both are identical methylmercapto, methylsulfinyl, methylsulfonyl or benzyloxy groups; and A is hydrogen;

or a non-toxic, pharmacologically acceptable acid addition salt thereof.

4. A compound of claim 1, wherein

R₁ is methyl, ethyl; benzyl; 1-phenyl-ethyl; 2-phenyl-ethyl; cyclohexyl; 4-chloro-phenyl; 2-methoxy-5-methylsulfonyl-phenyl; phenyl; or 2-and/or 4-mono- or di-substituted phenyl, where the substituents are each methoxy or hydroxyl, or one of them is methylmercapto, methylsulfinyl or methylsulfonyl, or both are identical methylmercapto, methylsulfinyl or methylsulfonyl groups; and A is hydrogen or

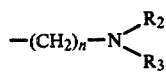

where

R₂ is hydrogen, methyl, ethyl or propyl;

R₃ is methyl, ethyl, propyl or 2-(3,4-dimethoxyphenyl-ethyl; or

R₂ and R₃, together with each other and the nitrogen atom to which they are attached are piperidino, morpholino or N'-lower alkyl-piperazino; and n is 2 or 3;

or a non-toxic, pharmacologically acceptable acid addition salt thereof.

5. A compound of claim 4, which is 7,7-dimethyl-2-phenyl-5-(2-dimethylamino-ethyl)-5H,7H-imidazo[4,5-h]isoquinoline-4,6-dione or a non-toxic, pharmacologically acceptable acid addition salt thereof.

6. A compound of claim 4, which is 7,7-dimethyl-2-phenyl-5-(3-diethylamino-propyl)-5H,7H-imidazo[4,5-h]isoquinoline-4,6-dione or a non-toxic, pharmacologically acceptable acid addition salt thereof.

7. A compound of claim 4, which is 7,7-dimethyl-2-phenyl-5-(3-piperidino-propyl)-5H,7H-imidazo[4,5-h]isoquinoline-4,6-dione or a none-toxic, pharmacologically acceptable acid addition salt thereof.

8. A compound of claim 4, which is 7,7-dimethyl-2-phenyl-5-(2-dimethylamino-ethyl)-5H,7H-imidazo[4,5-h]isoquinoline-4,6-dione or a non-toxic, pharacologically acceptable acid addition salt thereof.

9. A cardiotonic or hypotensive pharmaceutical dosage unit composition consisting essentially of an inert pharmaceutical carrier and an effective cardiotonic or hypotensive amount of a compound of claim 3.

10. An antiarrhythmic pharmaceutical dosage unit composition consisting essentially of an inert pharmaceutical carrier and an effective antiarrhythmic amount of a compound of claim 2.

11. The method of treating cardiac insufficiency or hypertension in a warm-blooded animal in need thereof, which comprises perorally, parenterally or rectally administering to said animal an effective cardiotonic or hypotensive amount of a compound of claim 3.

12. The method of treating cardiac arrhythmia in a warm-blooded animal in need thereof, which comprises perorally, parenterally or rectally administering to said animal an effective antiarrhythmic amount of a compound of claim 2.

* * * * *

UNITED STATES PATENT AND TRADEMARK OFFICE
CERTIFICATE OF CORRECTION

PATENT NO. : 4,176,184  Page 1 of 4
DATED : November 27, 1979
INVENTOR(S) : VOLKHARD AUSTEL ET AL.

It is certified that error appears in the above-identified patent and that said Letters Patent are hereby corrected as shown below:

Column 2, line 28: "sulfinyl-phe" should read -- sulfinylphe -- .

Column 4, line 30: "reducting" should read -- reducing --, line 61: "hydrochloride acid" should read -- hydrochloric acid --.

Column 5, line 19: "methylsulfornyl" should read -- methylsulfonyl --;

line 32: "such a" should read -- such as --, line 51: "furmaric acid", second occurrence, should be cancelled.
"furmaric acid" should read -- fumaric acid --.

Column 7, line 28: "hydrochlorice" should read -- hydrochloride --.

Column 8, line 42: "methyl-mercapto" should read -- methylmercapto --, line 68: "93%" should read -- 93.6% --.

Column 10, line 24: "phenyl-acetylamino" should read -- phenylacetylamino --.

Column 11, line 18: "5H-7H" should read -- 5H, 7H --

UNITED STATES PATENT AND TRADEMARK OFFICE
CERTIFICATE OF CORRECTION

PATENT NO. : 4,176,184
DATED : November 27, 1979
INVENTOR(S) : Volkhard Austel et al.

It is certified that error appears in the above-identified patent and that said Letters Patent are hereby corrected as shown below:

Column 11, line 31: "metylmercap" should read -- methylmercap --, line 64: "chlorform" should read -- chloroform --.

Column 12, line 24: "dion" should read -- dione --.

Column 13, line 38: "dihycro-" should read -- dihydro- --, line 62: "imidzao" should read -- imidazo --.

Column 14, line 47: "phaes" should read -- phases --, line 55: "5H-7H" should read -- 5H,7H --.

Column 16, line 21: "-imidazo-[" should read -- -imidazo[ --, line 38: "4,6,dione" should read -- 4,6-dione --, line 51: "5H-7H" should read -- 5H,7H --.

Column 17, line 37: "imidkazo" should read -- imidazo --, line 38: "difumerate" should read -- difumarate --.

Column 18, line 28: "[4,5-" should read -- [4,5-h] --, line 29: "hisoquinoline" should read -- isoquinoline.

Column 19, line 1: "PVA" should read -- PVC --,

UNITED STATES PATENT AND TRADEMARK OFFICE
CERTIFICATE OF CORRECTION

PATENT NO. : 4,176,184
DATED : November 27, 1979
INVENTOR(S) : VOLKHARD AUSTEL ET AL.

It is certified that error appears in the above-identified patent and that said Letters Patent are hereby corrected as shown below:

Column 19, line 44: "CaCl" should read -- $CaCl_2$ --.

Column 20, Table III, last line: "26.0%" should be deleted.

Table III, last column, on the level of "Q" and below "8.1%", it should read -- 26.0% --.

Column 21, line 20: "angino" should read -- angina --, line 23: "peorally" should read -- perorally --, line 27: "tables" should read -- tablets -- line 37: "activie" should read -- active --.

Column 23, line 14: "ampules" should read -- ampule --, line 54: "achiev" should read -- achieve --.

Column 25, line 24" "nyl-ethyl" should read -- nyl) ethyl --,

UNITED STATES PATENT AND TRADEMARK OFFICE
CERTIFICATE OF CORRECTION

PATENT NO. : 4,176,184
DATED : November 27, 1979
INVENTOR(S) : VOLKHARD AUSTEL ET AL.

It is certified that error appears in the above-identified patent and that said Letters Patent are hereby corrected as shown below:

Column 25, line 2 of Claim 5: "dimethylamino" should read -- diethylamino --.

Signed and Sealed this

Third Day of June 1980

[SEAL]

Attest:

SIDNEY A. DIAMOND

Attesting Officer

Commissioner of Patents and Trademarks